US009719966B2

United States Patent
Inagaki et al.

(10) Patent No.: US 9,719,966 B2
(45) Date of Patent: Aug. 1, 2017

(54) ULTRASONIC FLAW DETECTING APPARATUS, ULTRASONIC TRANSDUCER, AND ULTRASONIC FLAW DETECTING METHOD (71) Applicant: IHI Corporation, Tokyo (JP)

(72) Inventors: Koichi Inagaki, Tokyo (JP); Mamoru Izumi, Tokyo (JP); Hirokazu Karasawa, Kanagawa (JP)

(73) Assignee: IHI Corporation, Tokyo (JP)

( * ) Notice: Subject to any disclaimer, the term of this patent is extended or adjusted under 35 U.S.C. 154(b) by 366 days.

(21) Appl. No.: 14/093,166

(22) Filed: Nov. 29, 2013

(65) Prior Publication Data

US 2014/0083193 A1 Mar. 27, 2014

Related U.S. Application Data (63) Continuation of application No. 13/880,510, filed as application No. PCT/JP2011/074303 on Oct. 21, 2011, now abandoned.

(30) Foreign Application Priority Data

Oct. 22, 2010 (JP) .................................. 2010-237649

(51) Int. Cl.
G01N 29/04 (2006.01)
G01N 29/06 (2006.01)
(Continued)

(52) U.S. Cl.
CPC ........... *G01N 29/04* (2013.01); *G01N 29/069* (2013.01); *G01N 29/07* (2013.01); *G01N 29/223* (2013.01);
(Continued)

(58) Field of Classification Search
USPC .................. 73/640, 628, 629, 632, 633, 644
See application file for complete search history.

(56) References Cited

U.S. PATENT DOCUMENTS 5,465,722 A    11/1995 Fort et al.
6,009,755 A *  1/2000 Manome et al. ............... 73/602
(Continued)

FOREIGN PATENT DOCUMENTS

CN    1809748 A    7/2006
CN    101352354 A   1/2009
(Continued)

OTHER PUBLICATIONS

Office Action issued on Jan. 30, 2014 in the counterpart Russian Application No. 2013122839/28(033734) with English Translation).

(Continued)

*Primary Examiner* — Paul West
*Assistant Examiner* — Xin Zhong
(74) *Attorney, Agent, or Firm* — Oblon, McClelland, Maier & Neustadt, L.L.P.

(57) ABSTRACT

A transducer main body has, on a front end side thereof, an oscillating plane having a bent shape in a side view and corresponding to a larger-diameter curved surface formed at a bend of a laminated part. Over the oscillating plane of the transducer main body, a plurality of piezoelectric oscillators is distributed in a matrix in a bent direction and a width direction. In each oscillator group, a controlling unit switches the piezoelectric oscillators to transmission and reception piezoelectric oscillators by turns in the width direction according to a preset transmission/reception pattern and processes a received signal from the reception piezoelectric oscillator according to an aperture synthesis method.

8 Claims, 7 Drawing Sheets

(51) Int. Cl.
*G01N 29/07* (2006.01)
*G01N 29/22* (2006.01)

(52) U.S. Cl.
CPC ............... *G01N 2291/0231* (2013.01); *G01N 2291/106* (2013.01)

(56) References Cited

U.S. PATENT DOCUMENTS

| | | | |
|---|---|---|---|
| 2004/0016299 | A1 | 1/2004 | Glascock et al. |
| 2006/0123912 | A1 | 6/2006 | Karasawa et al. |
| 2006/0241464 | A1* | 10/2006 | Ohtake et al. ................ 600/457 |
| 2007/0227249 | A1* | 10/2007 | Meier et al. .................... 73/628 |
| 2009/0211361 | A1 | 8/2009 | Young et al. |

FOREIGN PATENT DOCUMENTS

| | | |
|---|---|---|
| CN | 101852773 A | 10/2010 |
| EP | 2 182 352 A2 | 5/2010 |
| JP | 57 75640 | 5/1982 |
| JP | 58 17361 | 2/1983 |
| JP | 61-96454 | 5/1986 |
| JP | 6 18488 | 1/1994 |
| JP | 6-339479 | 12/1994 |
| JP | 9 154844 | 6/1997 |
| JP | 2003 90829 | 3/2003 |
| JP | 2005 31061 | 2/2005 |
| JP | 2007 192649 | 8/2007 |
| JP | 2010 107286 | 5/2010 |
| WO | WO 99/48621 A2 | 9/1999 |
| WO | 2010 005647 | 1/2010 |
| WO | WO 2010/107637 A2 | 9/2010 |

OTHER PUBLICATIONS

Combined Office Action and Search Report issued Jul. 18, 2014 in Chinese Patent Application No. 201180050375.3 (with English Translation of category of Cited Documents).
International Search Report Issued Nov. 22, 2011 in PCT/JP11/74303 Filed Oct. 21, 2011.
Office Action issued Apr. 7, 2015 in Japanese Patent Application No. 2010-237649 (with English translation).
Extended European Search Report dated May 23, 2016, issued in EP Application No. 11834478.7, Eight (8) pages.
Abstract entitled "Flexible Ultrasonic Array System for Inspecting Thick Composite Structures", by Robert S. Frankle and Douglas N. Rose; SPIE vol. 2459/51-59; Nine (9) pages; Downloaded from: http://proceedings.spiedigitallibrary.org.

* cited by examiner

ULTRASONIC FLAW DETECTING APPARATUS, ULTRASONIC TRANSDUCER, AND ULTRASONIC FLAW DETECTING METHOD

CROSS REFERENCE TO RELATED APPLICATIONS

This application is a continuation of U.S. application Ser. No. 13/880,510 filed Apr. 19, 2013, the entire contents of which is incorporated herein by reference. U.S. application Ser. No. 13/880,510 is a National Stage of PCT/JP11/074,303 filed Oct. 21, 2011, which is based upon and claims the benefit of priority from prior Japanese Patent Application No. 2010-237649 filed Oct. 22, 2010.

TECHNICAL FIELD

The present invention relates to an ultrasonic flaw detecting apparatus for detecting an internal defective state at a bend of a laminated part made of composite materials, an ultrasonic transducer that is a principal component of the ultrasonic flaw detecting apparatus, and the like.

BACKGROUND ART

When detecting an internal defective state at a bend of a laminated part made of composite materials such as fiber-reinforced plastics (FRP), an ultrasonic transducer that transmits and receives ultrasonic waves is usually used.

The ultrasonic transducer has a transducer main body that has, on a front end side thereof, an oscillating plane having a bent shape in a side view and corresponding to a larger or smaller diameter curved surface formed at the bend of the laminated part. The oscillating plane of the transducer main body has a plurality of oscillators arranged in a bent direction of the oscillating plane of the transducer main body. Each oscillator transmits an ultrasonic wave toward the bend of the laminated part and receives a reflected wave from the bend of the laminated part. The oscillators are electrically connected to a controlling unit.

When detecting an internal defective state at the bend of the laminated part, the ultrasonic transducer is moved relative to the laminated part so that the oscillating plane of the transducer main body faces the larger or smaller diameter curved surface formed at the bend of the laminated part. The plurality of oscillators transmit ultrasonic waves toward the bend of the laminated part and receive reflected waves from the bend of the laminated part. According to received signals from the plurality of oscillators (flaw detecting signals from the ultrasonic transducer), the controlling unit nondestructively detects an internal defective state at the bend of the laminated part.

Related arts concerning the present invention are disclosed in, for example, Japanese Unexamined Patent Application Publications No. 2003-90829 and No. H06-18488.

SUMMARY OF INVENTION

Problems to be Solved by Invention

If the number of layers of the laminated part is increased, the bend of the laminated part becomes thicker. Then, the intensity of reflected ultrasonic waves becomes weaker, so that the ultrasonic transducer may insufficiently detect the reflected waves from an internal defect at the bend of the laminated part. To deal with this, a reflected-wave detecting sensitivity of the oscillators may be increased. This, however, results in increasing noise echoes to deteriorate an S/N ratio (a ratio of defect echoes to noise echoes) of flaw detecting signals from the ultrasonic transducer (received signals from the oscillators).

There is, therefore, a problem that a detecting accuracy of an internal defective state at a bend of a laminated part will not improve if the number of layers of the laminated part is increased to thicken the bend of the laminated part.

The present invention provides an ultrasonic flaw detecting apparatus, an ultrasonic transducer, and the like capable of realizing a high S/N ratio and improving a flaw detecting accuracy.

Means to Solve Problem

According to a first aspect of the present invention, the ultrasonic flaw detecting apparatus for detecting an internal defective state at a bend (curved portion) of a laminated part made of composite materials includes an ultrasonic transducer that transmits and receives ultrasonic waves and a controlling unit that, according to flaw detecting signals (received signals) from the ultrasonic transducer, detects and processes the internal defective state at the bend of the laminated part. In more detail, the ultrasonic transducer includes a transducer main body that has, on a front end side thereof, an oscillating plane having a bent shape in a side view and corresponding to a larger- or smaller-diameter curved surface formed at the bend of the laminated part and a plurality of oscillators distributed over the oscillating plane in a matrix in a bent direction (curved direction) of the oscillating plane of the transducer main body and a width direction of the transducer main body (i.e., a direction orthogonal to a side face of the transducer main body), to transmit ultrasonic waves toward the bend of the laminated part and receive reflected waves from the bend of the laminated part. The controlling unit successively carries out, for each oscillator group formed of a width-direction row of the plurality of oscillators, switching the oscillators in the oscillator group to oscillators for transmission and reception by turns in the width direction according to a preset transmission/reception pattern and processing a received signal from the reception oscillator according to an aperture synthesis method.

In the descriptions of the specification and claims of this application, the "internal defective state" means the presence or absence of an internal defect, the size and location of the internal defect, and the like. The "bent shape in a side view corresponding to a curved surface" means a shape that extends along a curved surface and is bent when seen from a side thereof, or a shape that extends along an inversion of the curved surface. The "transmission oscillator" is one selected from the oscillators, to transmit an ultrasonic wave and the "reception oscillator" is one selected from the oscillators, to receive a reflected wave.

According to a second aspect of the present invention, the ultrasonic transducer for use in detecting an internal defective state at a bend (curved portion) of a laminated part made of composite materials by transmitting and receiving ultrasonic waves includes a transducer main body that has, on a front end side thereof, an oscillating plane having a bent shape in a side view and corresponding to a larger- or smaller-diameter curved surface formed at the bend of the laminated part and a plurality of oscillators distributed over the oscillating plane in a matrix in a bent direction of the oscillating plane of the transducer main body and a width direction of the transducer main body, i.e., a direction orthogonal to a side face of the transducer main body, to transmit ultrasonic waves toward the bend of the laminated part and receive reflected waves from the bend of the laminated part.

According to a third aspect of the present invention, the ultrasonic flaw detecting method of detecting, with the use of the ultrasonic transducer of the second aspect, an internal defective state at a bend (curved portion) of a laminated part made of composite materials includes moving the ultrasonic transducer relative to the laminated part so that the oscillating plane of the transducer main body faces a larger- or smaller-diameter curved surface formed at the bend of the laminated part, interposing an acoustic medium between the bend of the laminated part and the ultrasonic transducer, grouping each row in the width direction of the plurality of oscillators into an oscillator group, switching the oscillators in a given one of the oscillator groups to oscillators for transmission and reception by turns in the width direction according to a preset transmission/reception pattern, transmitting an ultrasonic wave from the transmission oscillator into the bend of the laminated part, receiving a reflected wave from the bend of the laminated part with the reception oscillator, processing a received signal from the reception oscillator according to an aperture synthesis method, successively carrying out, for each of the remaining oscillator groups, switching the transmission and reception oscillators from one to another in the width direction among the oscillators in the oscillator group, and processing a received signal from the reception oscillator according to the aperture synthesis method, thereby detecting the internal defective state at the bend of the laminated part.

BRIEF DESCRIPTION OF DRAWINGS

FIG. 3($a$) is a view taken along a line IIIB-IIIB of FIG. 4($b$) and FIG. 3($b$) is a developed plan view of an oscillating plane on a transducer main body of the ultrasonic transducer according to the embodiment of the present invention.

FIG. 4($a$) is a front view of the ultrasonic transducer according to the embodiment of the present invention and FIG. 4($b$) is a side view of the ultrasonic transducer according to the embodiment of the present invention.

DESCRIPTION OF THE PREFERRED EMBODIMENT

Embodiments of the present invention will be explained with reference to FIGS. 1 to 7.

Figure 7:
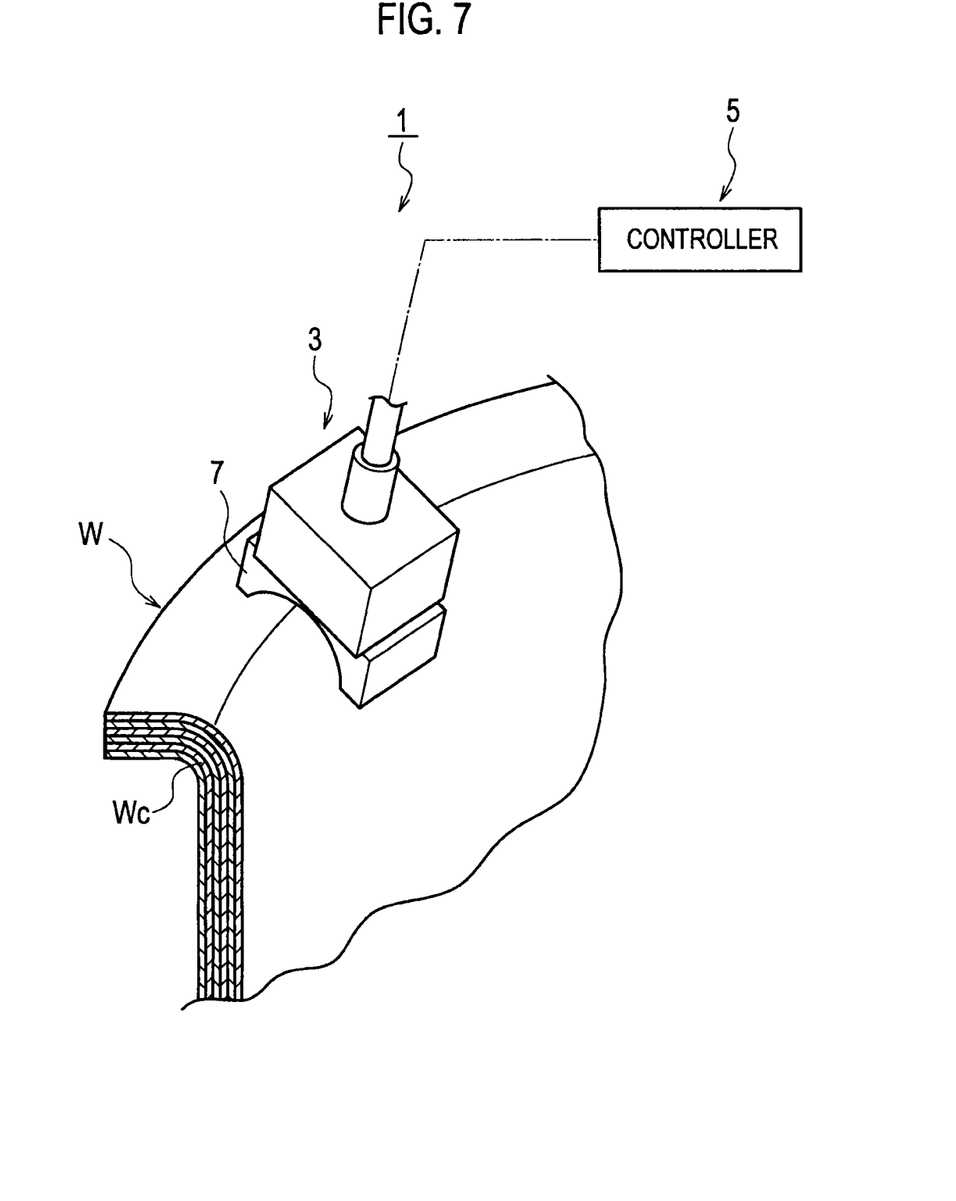
FIG. 7 is a perspective view generally illustrating the ultrasonic flaw detecting apparatus according to the embodiment of the present invention.

As illustrated in FIG. 7, an ultrasonic flaw detecting apparatus 1 according to an embodiment of the present invention detects an internal defective state at a bend (curved portion) Wc of a laminated part W made of composite materials and includes an ultrasonic transducer 3 that transmits and receives ultrasonic waves S (refer to FIG. 2) through an acoustic medium M and a controlling unit that, according to flaw detecting signals from the ultrasonic transducer 3, detects and processes the internal defective state at the bend Wc of the laminated part W. The laminated part W of the embodiment of the present invention is an airplane part such as a casing made of fiber-reinforced plastics (FRP), the bend Wc of the laminated part W is a base of a flange of the casing, and the acoustic medium M is a liquid such as water, or a solid.

The details of a configuration of the ultrasonic transducer 3 according to an embodiment of the present invention will be explained.

As illustrated in FIGS. 1 to 4, the ultrasonic transducer 3 has a transducer main body 7. The transducer main body 7 has, on a front end side thereof, an oscillating plane 9 that has a bent shape in a side view to follow a larger-diameter curved surface formed at the bend Wc of the laminated part W. Instead of the oscillating plane 9 having the bent shape in a side view to follow the larger-diameter curved surface formed at the bend Wc of the laminated part W, the transducer main body 7 may have an oscillating plane having a shape to follow a smaller-diameter curved surface formed at the bend Wc of the laminated part W.

Over the oscillating plane 9 of the transducer main body 7, a plurality (8×8 pieces according to the embodiment of the present invention) of piezoelectric oscillators 11 are distributed in a matrix manner in a bent direction AD of the oscillating plane 9 of the transducer main body 7 and a width direction of the transducer main body 7, i.e., a direction BD orthogonal to a side face of the transducer main body 7. Each of the piezoelectric oscillators 11 transmits an ultrasonic wave S toward the bend Wc of the laminated part W and receives a reflected wave S from the bend Wc of the laminated part W. Each piezoelectric oscillator 11 is made of composite materials or ceramics and is connected to the controlling unit 5. According to the embodiment of the present invention, eight piezoelectric oscillators 11 arranged in the width direction BD form a piezoelectric oscillator group 11G, and therefore, there are eight piezoelectric oscillator groups 11G.

Inside the transducer main body 7, there is arranged a damper (not illustrated) to absorb excessive oscillations of the piezoelectric oscillators 11.

The details of the controlling unit 5 according to the embodiment of the present invention will be explained.

Figure 1:
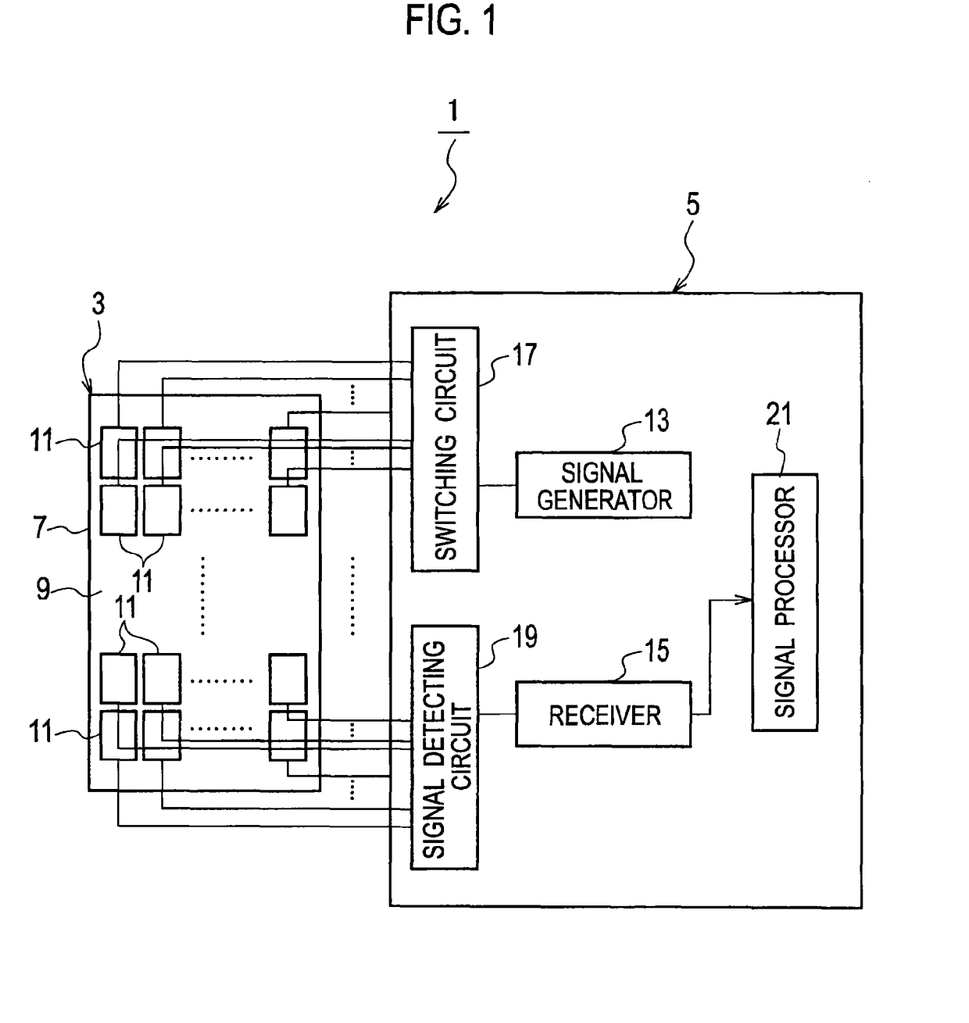
FIG. 1 is a control block diagram of an ultrasonic flaw detecting apparatus according to an embodiment of the present invention.
Figure 2:
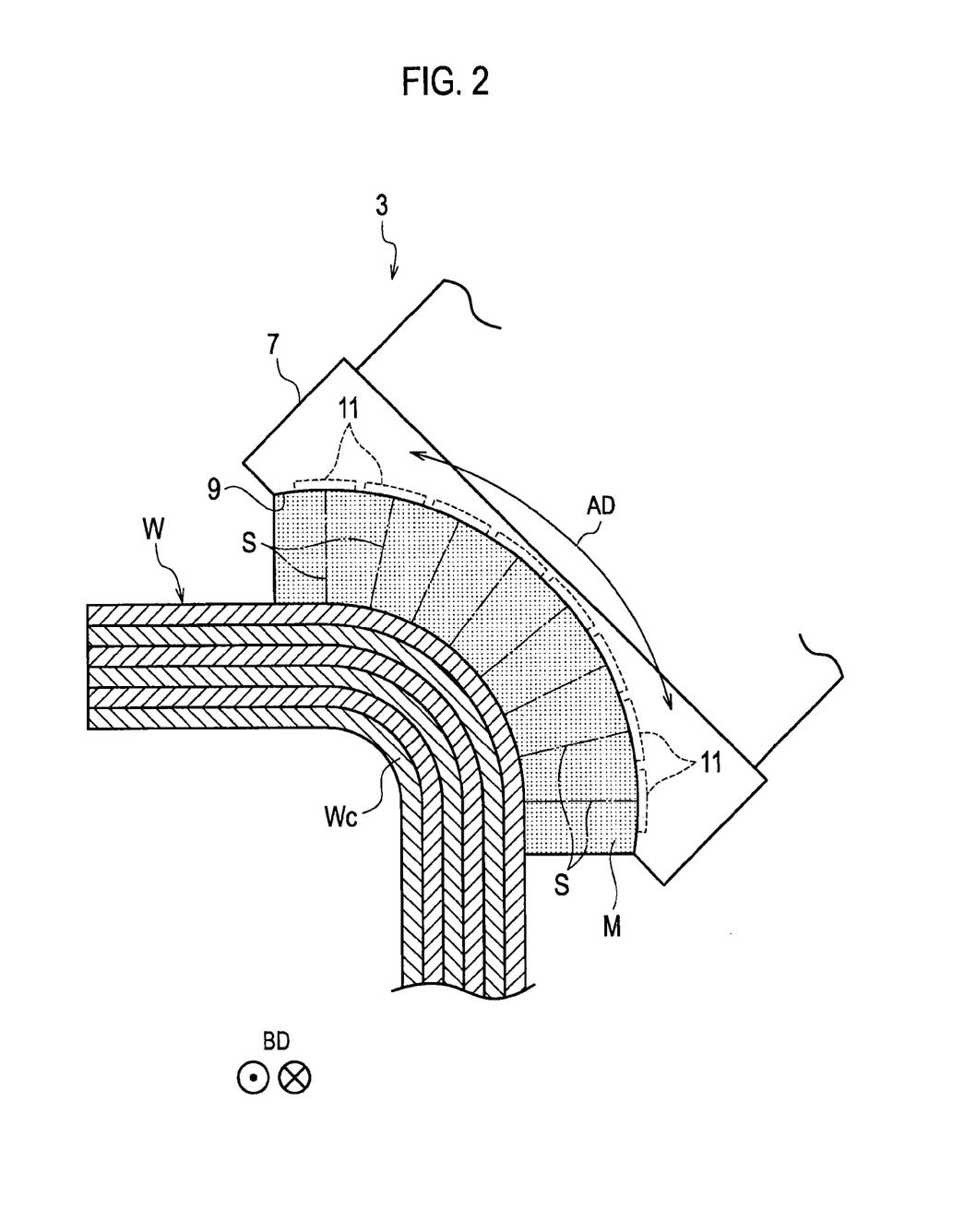
FIG. 2 is an enlarged side view of an ultrasonic transducer according to an embodiment of the present invention.
Figure 3:
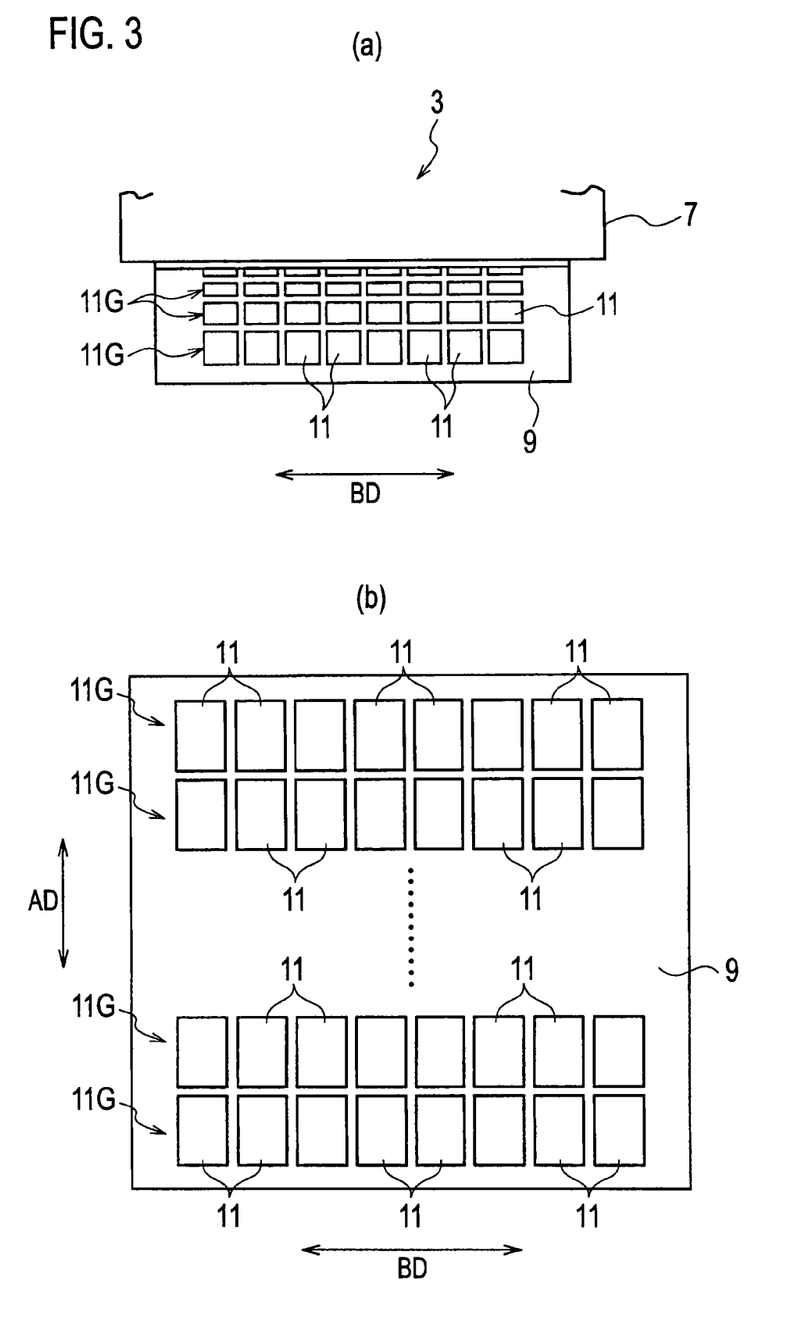
Figure 4:
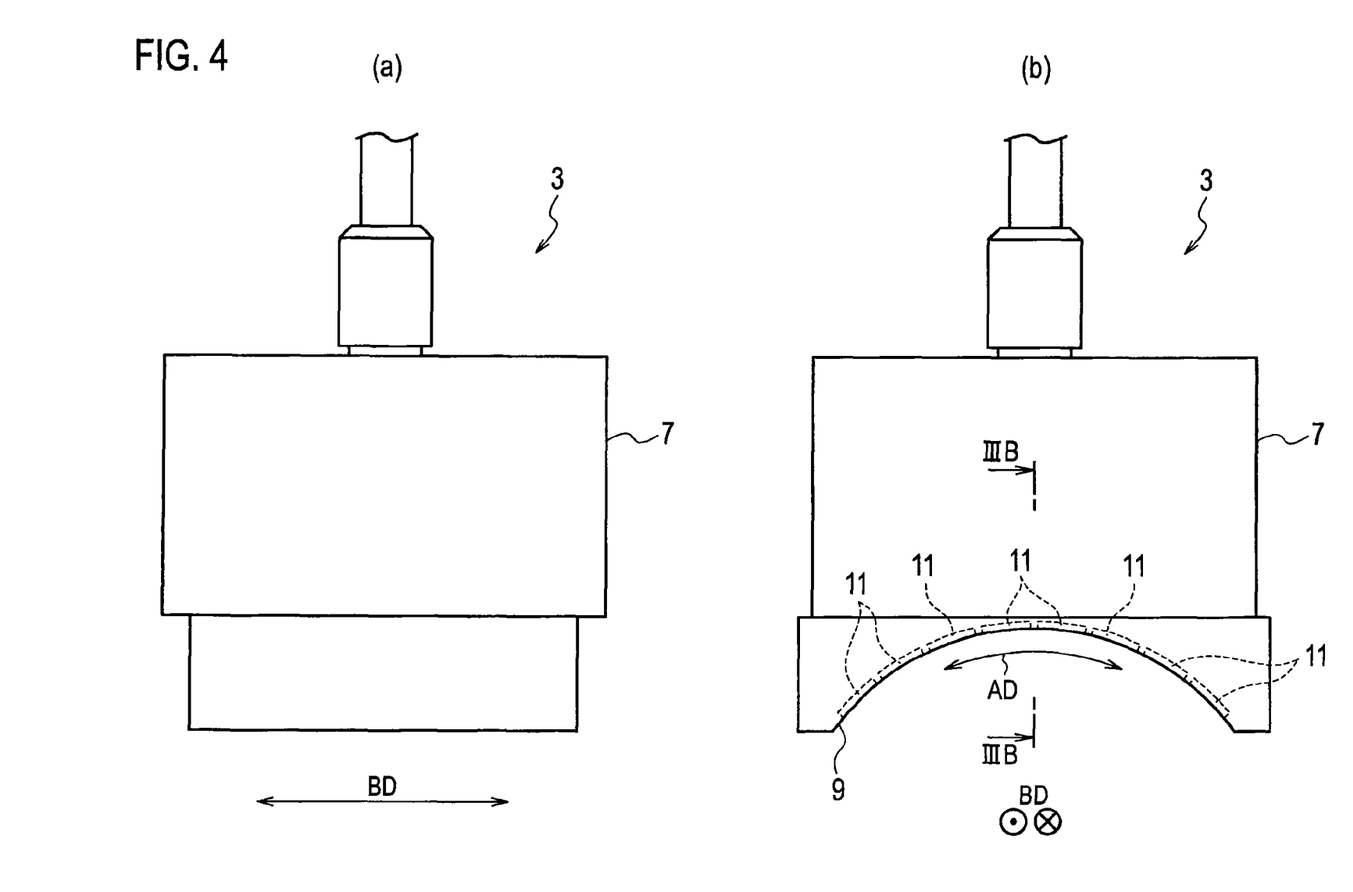

As illustrated in FIG. 1, the controlling unit 5 has a signal generating unit 13 that supplies a drive signal (a transmission signal) to the piezoelectric oscillators 11 and a receiver 15 that amplifies received signals from the piezoelectric oscillators 11 (flaw detection signals from the ultrasonic transducer 3). The signal generating unit and piezoelectric oscillators 11 are connected to a switching circuit 17. The switching circuit 17 is capable of switching a selected one of the piezoelectric oscillators and the signal generating unit 13 to a connected state and a disconnected state. The receiver 15 and piezoelectric oscillators 11 are connected to a signal detecting circuit 19. The signal detecting circuit 19 is capable of switching a selected one of the piezoelectric oscillators 11 and the receiver 15 to a connected state and a disconnected state.

Figure 5:
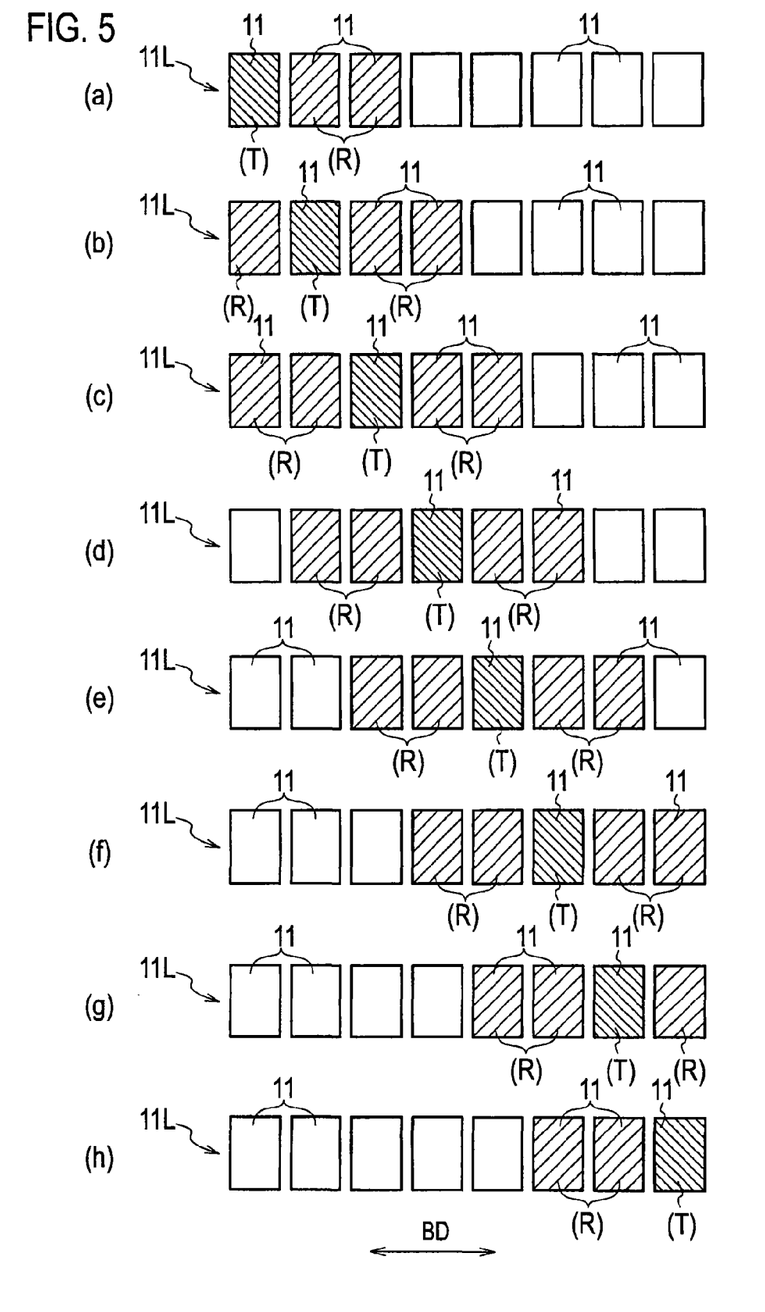
FIG. 5 is a view explaining switching piezoelectric oscillators to transmission and reception piezoelectric oscillators according to a first transmission/reception pattern.

More precisely, as illustrated in FIG. 5, the switching circuit 17 sequentially switches the piezoelectric oscillators 11 in each piezoelectric oscillator group 11G to a transmission piezoelectric oscillator 11 (T) in eight steps in the width direction BD by use of a preset first transmission/reception pattern. Similarly, the signal detecting circuit 19 uses the first transmission/reception pattern to sequentially switch between the piezoelectric oscillators 11 in each piezoelectric oscillator group 11G to reception piezoelectric oscillators 11 (R) in eight steps in the width direction BD.

Figure 6:
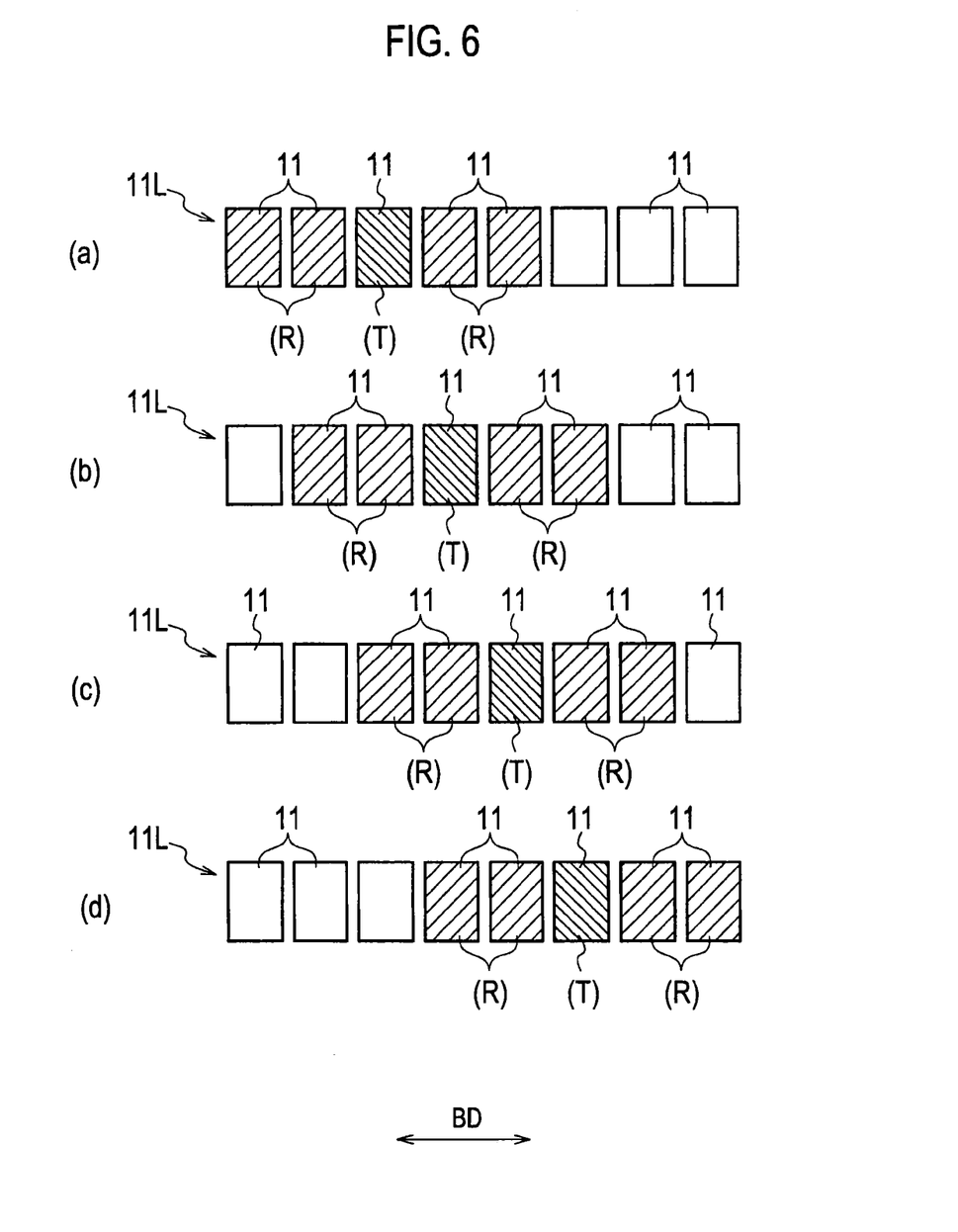
FIG. 6 is a view explaining switching the piezoelectric oscillators to transmission and reception piezoelectric oscillators according to a second transmission/reception pattern.

Instead of the first transmission/reception pattern, a preset second transmission/reception pattern illustrated in FIG. 6 may be used to sequentially switch between the piezoelectric oscillators 11 in each piezoelectric oscillator group 11G to transmission and reception piezoelectric oscillators 11 (transmission piezoelectric oscillator 11 and reception piezoelectric oscillators 11) in four steps in the width direction BD. When the second transmission/reception pattern is used, the transmission piezoelectric oscillator 11 is located in an intermediate area in the width direction BD on the oscillating plane 9 of the transducer main body 7 and the reception piezoelectric oscillators 11 (R) sandwich the transmission piezoelectric oscillator 11 (T) from each side in the width direction BD.

The receiver 15 is connected to a signal processing unit 21. The signal processing unit 21 successively processes received signals, which are received by the reception piezoelectric oscillators 11 and are amplified, according to an aperture synthesis method (a superposing process). The aperture synthesis method uses system information pieces such as a positional relationship between the ultrasonic transducer 3 and the bend Wc of the laminated part W, a flaw detecting frequency of the ultrasonic transducer 3, acoustic velocities in the laminated part W and acoustic medium M, and the like. The signal processing unit 21 is connected to a display unit (not illustrated) that combines a process result (such as an aperture synthesis image) of the signal processing unit 21 with the positional information of the transducer 3 and displays a combined result.

An ultrasonic flaw detecting method according to an embodiment of the present invention and effect thereof will be explained.

The ultrasonic transducer 3 is moved relative to the laminated part W so that the oscillating plane 9 of the transducer main body 7 faces the large-diameter curved surface formed at the bend Wc of the laminated part W. With the acoustic medium M interposed between the bend Wc of the laminated part W and the ultrasonic transducer 3, an ultrasonic wave S is transmitted from a transmission piezoelectric oscillator 11 and is made incident to the bend Wc of the laminated part W, and a reflected wave S is received by a reception piezoelectric oscillator 11. In more detail, the switching circuit 17 and signal detecting circuit 19 are used to sequentially switch between the piezoelectric oscillators 11 in a given piezoelectric oscillator group 11G to transmission and reception piezoelectric oscillators 11 in eight or four steps in the width direction BD according to the first or second transmission/reception pattern (refer to FIGS. 5 and 6). In each step, an ultrasonic wave S transmitted from the transmission piezoelectric oscillator 11 is made incident to the bend Wc of the laminated part W and a reflected wave S from the bend Wc of the laminated part W is received by the reception piezoelectric oscillator 11 (refer to FIG. 2). With respect to received signals from the reception piezoelectric oscillators 11 in the given piezoelectric oscillator group 11G, the aperture synthesis method is carried out by the signal processing unit 21.

Similarly, in each of the remaining piezoelectric oscillator groups 11G, the switching circuit 17 and signal detecting circuit 19 are used to sequentially switch between the piezoelectric oscillators 11 to transmission and reception piezoelectric oscillators 11 in eight or four steps in the width direction BD according to the first or second transmission/ reception pattern. With respect to received signals from the reception piezoelectric oscillators 11, the aperture synthesis method is successively carried out by the signal processing unit 21. In this way, for a circumferential partial area of the bend Wc of the laminated part W, the controlling unit 5 conducts a detecting process (a flaw detecting process) of detecting an internal defective state (the presence or absence of an internal defect, the size and location of the internal defect, and the like), thereby testing the internal defective state (finding flaws).

After detecting the internal defective state in the circumferential partial detection area at the bend Wc of the laminated part W, the ultrasonic transducer 3 is moved in a circumferential direction along the laminated part W and the processes mentioned above are repeated, to detect an internal defective state in the whole circumferential area at the bend Wc of the laminated part W.

Since the plurality of piezoelectric oscillators 11 are distributed over the oscillating plane 9 of the transducer main body 7 in a matrix manner in the bend direction AD and width direction BD, the switching circuit 17 and signal detecting circuit 19 can switch between the piezoelectric oscillators 11 in each piezoelectric oscillator group 11G to piezoelectric oscillators 11 for transmission and reception. And the signal processing unit 21 can carry out the aperture synthesis method on received signals from the piezoelectric oscillators 11 for reception in each piezoelectric oscillator group 11G. Even if the number of layers of the laminated part W is increased to thicken the bend Wc of the laminated part W, the ultrasonic transducer 3 can sufficiently and surely detect reflected waves S representing an internal defect at the bend W of the laminated part W without increasing a detective sensitivity on reflected waves S received by the piezoelectric oscillators 11 for reception.

Accordingly, the embodiment of the present invention is capable of reducing noise echoes, heightening an S/N ratio of flaw detecting signals from the ultrasonic transducer 3 (received signals from reception piezoelectric oscillators 11), and improving a detecting accuracy (a flaw detecting accuracy) of an internal defective state at the bend Wc of the laminated part W even if the number of layers of the laminated part W is increased to thicken the bend Wc of the laminated part W.

Particularly when based on the second transmission/ reception pattern illustrated in FIG. 6, the embodiment is capable of limiting a detecting area (a flaw detecting area) of the ultrasonic transducer 3 and carrying out the aperture synthesis method on received signals from reception piezoelectric oscillators 11 used to receive reflected waves S, thereby improving a detecting accuracy of an internal defective state at the bend Wc of the laminated part W.

As mentioned above, the first and second aspects of the present invention move the ultrasonic transducer relative to a laminated part so that the oscillating plane of the transducer main body faces a larger- or smaller-diameter curved surface at a bend of the laminated part. Thereafter, the controlling unit switches between the oscillators in a given oscillator group to oscillators for transmission and reception in the width direction of the transducer according to a transmission/reception pattern, transmits an ultrasonic wave from the transmission oscillator into the bend of the laminated part, and receives a reflected wave from the bend of the laminated part with the reception oscillator. Thereafter, the controlling unit carries out the aperture synthesis method on a received signal from the reception oscillator. In this way, the controlling unit achieves a detecting process of detecting an internal defective state at the bend of the laminated part, thereby finding the internal defective state at the bend of the laminated part.

In the ultrasonic transducer, the oscillators are distributed over the oscillating plane of the transducer main body in a matrix manner in the bent and width directions, and therefore, the controlling unit can switch between the oscillators in each oscillator group to oscillators for transmission and reception in the width direction according to a transmission/reception pattern and successively process received signals from the reception oscillators according to the aperture synthesis method. Even if the number of layers of the laminated part is increased to thicken the bend of the laminated part, the ultrasonic transducer can sufficiently and surely detect reflected waves representing an internal defect at the bend of the laminated part without increasing a detective sensitivity on the reflected waves received by the reception oscillators.

According to the third aspect of the present invention, the oscillators are distributed over the oscillating plane of the transducer main body of the ultrasonic transducer in a matrix manner in the bent and width directions. Accordingly, as mentioned above, the controlling unit can switch between the oscillators in each oscillator group to transmission and reception oscillators in the width direction according to a transmission/reception pattern and successively process received signals from the reception oscillators according to the aperture synthesis method. Even if the number of layers of the laminated part is increased to thicken the bend of the laminated part, the ultrasonic transducer can sufficiently and surely detect reflected waves representing an internal defect at the bend of the laminated part without increasing a detective sensitivity on the reflected waves received by the reception oscillators.

According to the present invention, even if the number of layers of the laminated part is increased to thicken the bend of the laminated part, the ultrasonic transducer can sufficiently and surely detect reflected waves representing an internal defect at the bend of the laminated part, and therefore, the present invention can reduce noise echoes, heighten an S/N ratio of flaw detecting signals from the ultrasonic transducer, and improve a detecting accuracy of an internal defective state at the bend of the laminated part.

The present invention is not limited to the above-mentioned embodiments but is achievable in various forms. The scope of right covered by the present invention is not limited by these embodiments.

UNITED STATES DESIGNATION

In connection with United States designation, this international patent application claims the benefit of priority under 35 U.S.C. 119(a) to Japanese Patent Application No. 2010-237649 filed on Oct. 22, 2010, the entire content of which is incorporated by reference herein.

What is claimed is:

1. An ultrasonic flaw detecting apparatus for detecting an internal defective state at a bend of a laminated part made of composite materials, comprising:
   an ultrasonic transducer transmitting and receiving ultrasonic waves; and
   a controlling unit configured to detect and process the internal defective state at the bend of the laminated part according to flaw detecting signals from the ultrasonic transducer, wherein:
   the ultrasonic transducer includes
      a transducer main body that has, on a front end side thereof, an oscillating plane having a bent shape in a side view and corresponding to an outer surface or an inner surface formed at the bend of the laminated part, and
      a plurality of oscillators that are distributed over the oscillating plane in a matrix manner in a bent direction of the oscillating plane of the transducer main body and a width direction of the transducer main body, and is configured to transmit ultrasonic waves toward the bend of the laminated part and receive reflected waves from the bend of the laminated part,
   the controlling unit successively carries out, for each oscillator group of the plurality of oscillators in which each oscillator group is formed of a row of the oscillators extending in the width direction, switching between the oscillators in the oscillator group to transmission and reception oscillators by turns in the width direction according to a preset transmission/reception pattern and processing a received signal from the reception oscillator according to an aperture synthesis method such that the transmission oscillator in each oscillator group sequentially moves in the row of the respective oscillator group along the width direction, and
   in the preset transmission/reception pattern, two consecutive reception oscillators are adjacent to the transmission oscillator on each side of the transmission oscillator in the width direction throughout the preset transmission/reception pattern, one of the two consecutive reception oscillators on each side being immediately adjacent to the transmission oscillator.

2. The ultrasonic flaw detecting apparatus according to claim 1, wherein
   the transmission oscillator is located in an intermediate area in the width direction on the oscillating plane of the transducer main body and the reception oscillators sandwich the transmission oscillator from each side in the width direction.

3. An ultrasonic flaw detecting method of detecting an internal defective state at a bend of a laminated part made of composite materials by use of an ultrasonic transducer, wherein
   the ultrasonic transducer transmits and receives ultrasonic waves, and comprises: a transducer main body having an oscillating plane on a front end side thereof, the oscillating plane having a bent shape in a side view and corresponding to an outer surface or an inner surface formed at the bend of the laminated part; and a plurality of oscillators distributed over the oscillating plane in a matrix manner in a bent direction of the oscillating plane of the transducer main body and a width direction of the transducer main body, configured to transmit ultrasonic waves toward the bend of the laminated part and receive reflected waves from the bend of the laminated part, the ultrasonic flaw detecting method comprising:
   moving the ultrasonic transducer relative to the laminated part so that the oscillating plane of the transducer main body faces the outer surface or the inner surface formed at the bend of the laminated part;
   interposing an acoustic medium between the bend of the laminated part and the ultrasonic transducer, grouping each row in the width direction of the plurality of oscillators into an oscillator group, switching between the oscillators in a given one of the oscillator groups to transmission and reception oscillators by turns in the width direction according to a preset transmission/reception pattern, transmitting an ultrasonic wave from the transmission oscillator into the bend of the laminated part, receiving a reflected wave from the bend of the laminated part with the reception oscillator, and processing a received signal from the reception oscillator according to an aperture synthesis method; and successively carrying out, for each of the remaining oscillator groups, switching the transmission and reception oscillators from one to another in the width direction among the oscillators in the oscillator group such that the transmission oscillator in each oscillator group sequentially moves in the row of the respective oscillator group along the width direction, and processing a received signal from the reception oscillator according to the aperture synthesis method, thereby detecting the internal defective state at the bend of the laminated part, wherein in the preset transmission/reception pattern, two consecutive reception oscillators are adjacent to the transmission oscillator on each side of the transmission oscillator in the width direction throughout the preset transmission/reception pattern, one of the two consecutive reception oscillators on each side being immediately adjacent to the transmission oscillator.

4. The ultrasonic flaw detecting method according to claim 3, wherein the laminated part is an airplane part made of fiber-reinforced plastics.

5. The ultrasonic flaw detecting method according to claim 3, wherein the acoustic medium is a liquid.

6. The ultrasonic flaw detecting method according to claim 3, wherein the acoustic medium is a solid.

7. The ultrasonic flaw detecting method according to claim 4, wherein the acoustic medium is a liquid.

8. The ultrasonic flaw detecting method according to claim 4, wherein the acoustic medium is a solid.

* * * * *